US00PP28103P2

(12) United States Plant Patent
Van Swieten

(10) Patent No.: US PP28,103 P2
(45) Date of Patent: Jun. 13, 2017

(54) *PHALAENOPSIS* ORCHID PLANT NAMED 'PHALFOYX'

(50) Latin Name: ***Phalaenopsis* hybrid**
Varietal Denomination: PHALFOYX

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 13 days.

(21) Appl. No.: 14/757,344

(22) Filed: Dec. 18, 2015

(51) Int. Cl.
*A01H 5/02* (2006.01)

(52) U.S. Cl.
USPC ..... Plt./311

(58) Field of Classification Search
USPC ..... Plt./311
See application file for complete search history.

(56) References Cited

PUBLICATIONS

Enclosure for the Plant Patent application of Anthura BV, 13 pages, 2015.

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALFOYX', particularly characterized by having white dotted and edged flowers (dots are larger at the base and become smaller towards the edge; number and intensity of spots depends on the temperature), 1 to 2 peduncles, an inflorescence that is long and sturdy, leaves that are ovate/oblong, and is propagated by meristem tissue culture, is disclosed.

3 Drawing Sheets

Genus and species: *Phalaenopsis* hybrid.
Variety denomination: 'PHALFOYX'.

BACKGROUND OF THE NEW PLANT

The present invention comprises a new and distinct cultivar of *Phalaenopsis* plant, botanically known as *Phalaenopsis* of the Orchidaceae family, and hereinafter referred to by the cultivar name 'PHALFOYX'.

*Phalaenopsis* comprises a genus of about 60 species of herbaceous perennials many of which, or the hybrids thereof, are suitable for cultivar in the home or greenhouse. *Phalaenopsis* is predominantly epiphytic or rock dwelling, and is native to tropical Asia, the Malay Archipelago, and Oceania. The species typically has 2-ranked, fleshy, oblong or elliptic leaves affixed to a short central stem (monopodial growth), which vary in size from 12 to 20 cm to over 60 cm. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petals, called the labellum, are three-lobed and are often more brightly-colored than the other flower segments. Flower colors include various shades of pink, white, yellow, and red-brown.

*Phalaenopsis* orchids are typically propagated from seeds. Asexual propagation of *Phalaenopsis* is often done from off-shoots which arise from the lower bracts of the inflorescence. The resulting plants are detached from the mother plants and may be planted in a suitable substrate.

The new *Phalaenopsis* 'PHALFOYX' is particularly characterized by its attractive and unique white dotted and edged flowers, economical propagation by tissue culture, rapid growth, and a plant dimension suitable for packaging and shipping to the market.

'PHALFOYX' is a product of a planned breeding program conducted by the inventor in Bleiswijk, The Netherlands.

The new *Phalaenopsis* 'PHALFOYX' originated from a cross made in July 2006 in Bleiswijk, The Netherlands. The female parent is an unknown *Phalaenopsis* pot plant named 'unknown' (unpatented), while the male parent is a white flecked *Phalaenopsis* pot plant named '00001-1920' (unpatented). A single plant was selected in July 2009 and has been asexually reproduced repeatedly by meristem tissue culture in Bleiswijk, The Netherlands over a 3.5-year period. The new variety has been found to retain its distinctive characteristics through successive asexual propagations.

Asexual reproduction of 'PHALFOYX' by tissue culture was first performed in May 2012 in Bleiswijk, The Netherlands and has demonstrated that the new cultivar is firmly fixed and retained through successive generations of asexual reproduction.

Plant Breeder's Rights for this variety have not been applied for. 'PHALFOYX' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands.

1) White dotted and edged flowers (dots are larger at the base and become smaller towards the edge; the number and intensity of dots depends on the temperature);
2) 1 to 2 peduncles;
3) Inflorescence is long and sturdy;
4) Shape of the leaf is ovate/oblong; and
5) Plants are propagated by meristem tissue culture.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs are of a 50-week old plant grown in a greenhouse in Bleiswijk, The Netherlands in August 2015.

DESCRIPTION OF THE NEW VARIETY

Figure 1:
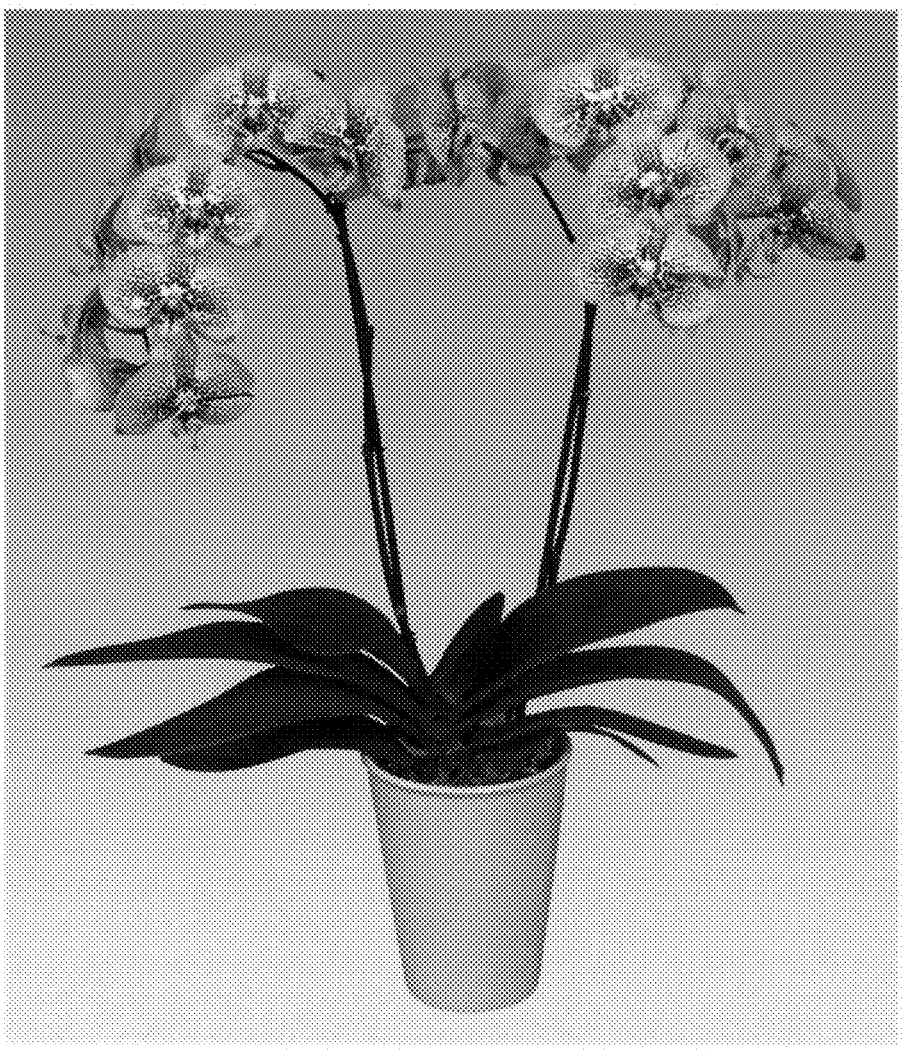
FIG. 1 shows the overall plant habit, including blooms and foliage of 'PHALFOYX'.
Figure 2:
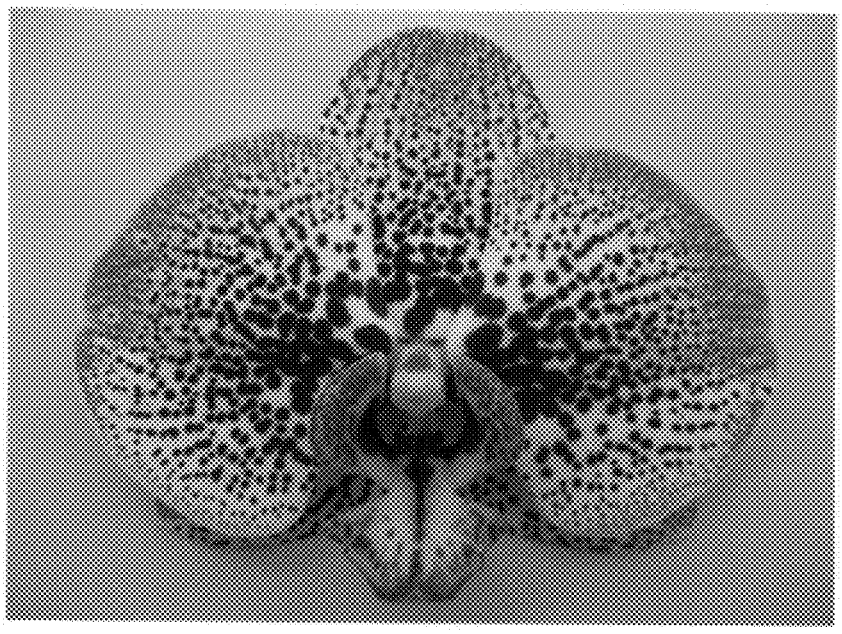
FIG. 2 shows a close-up of a flower of 'PHALFOYX'.
Figure 3:
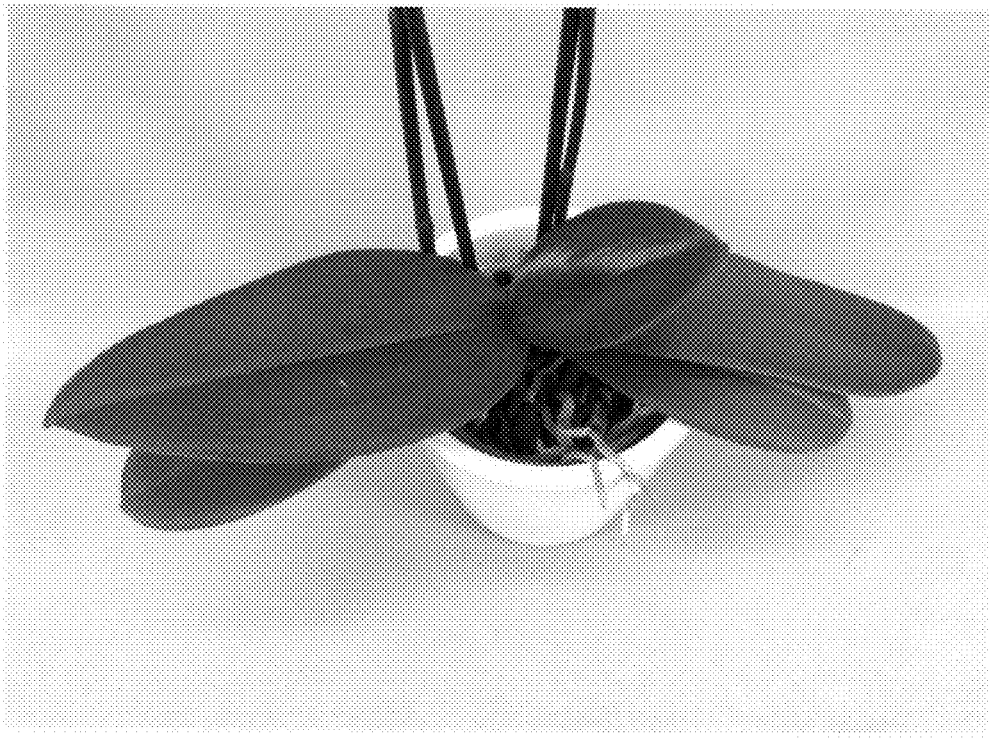
FIG. 3 shows a close-up of the leaves of 'PHALFOYX'.

The following detailed description sets forth the distinctive characteristics of 'PHALFOYX'. The data which define these characteristics were collected from asexual reproductions carried out in Bleiswijk, The Netherlands. The plant history was taken on 50-week old plants which were planted from a nursery tray in 12 centimeter pots and grown in a greenhouse between 27° C. to 29° C. for 30 weeks, continued by a cooling period of 8 weeks between 18° C. to 20° C. and 12 weeks in a greenhouse of 21° C. Observations were made in August 2015. Color readings were taken under 4-6000 lux natural light in the greenhouse. Color references are primarily to The R.H.S. Colour Chart of The Royal Horticultural Society of London (R.H.S.) (1995).

DETAILED BOTANICAL DESCRIPTION

Classification:

*Family.*—Orchidaceae.

*Botanical.*—*Phalaenopsis* hybrid.

*Common name.*—*Phalaenopsis.*

*Variety name.*—'PHALFOYX'.

Parentage:

*Female parent.*—*Phalaenopsis* cultivar 'unknown' (unpatented).

*Male parent.*—*Phalaenopsis* cultivar '00001-1920' (unpatented).

Propagation:

*Type.*—Meristem tissue culture.

Plant:

*Crop time* (*time to produce a finished flowering plant*).—48 to 50 weeks for a 12 cm pot.

*Growth habit of peduncle.*—Standard, green leaves, raceme to panicle.

*Height* (*including pot, including inflorescence*).—55.0 cm to 65.0 cm.

*Width* (*measured from leaf tips*).—34.0 cm to 39.0 cm.

*Vigor.*—Moderate.

Roots:

*Root description.*—Greyed-green colored roots with branching lateral roots having light purple colored root tips.

Leaves:

*Mature leaves.*—Quantity per plant: 7 to 9 leaves are produced before flowering. Length (fully expanded): 17.0 cm to 20.0 cm. Width: 7.5 cm to 8.5 cm. Shape: Obovate. Base shape: Moderately elongated. Apex: Unequal rounded/obtuse. Leaf blade angle with the petiole (measured from the horizontal position): Between 0 degrees and 30 degrees. Leaf margin: Entire. Color: Upper surface: RHS 146A/147A. Lower surface: RHS 147B with edge RHS 187A. Texture: Rough. Thickness: 2.6 mm to 2.8 mm. Venation: Pattern: Parallel. Color of the midvein: Upper surface: RHS 147A. Lower surface: RHS 187A.

Peduncle:

*Quantity per plant.*—1 to 2.

*Number of flowers per peduncle.*—7 to 12.

*Length.*—42.0 cm to 47.0 cm.

*Diameter.*—5.3 mm to 5.8 mm.

*Strength.*—Strong.

*Aspect.*—Upright to slightly pendant.

*Texture.*—Smooth.

*Color.*—Mix of brown (RHS 200A) with a touch of greyed-green (RHS 195A).

*Internode length.*—40.0 mm to 50.0 mm.

*Callosities.*—None.

Inflorescence description:

*Appearance.*—Upright to slightly pendant, raceme to panicle inflorescence with bilaterally symmetrical flowers that open in succession beginning with the lowermost flower.

*Inflorescence size.*—Height (from base to tip): 180.0 mm to 210.0 mm.

*Flowering time.*—First flowers can be expected 10 to 11 months after planting in a 12 cm pot.

*Flower.*—Height: 87.0 mm to 92.0 mm. Diameter: 90.0 mm to 100.0 mm. Depth of lip: 19.0 mm to 21.0 mm.

*Flower longevity.*—On the plant: 9 to 11 weeks.

*Fragrance.*—Absent.

*Flower bud.*—Average size: Medium. Length: 18.0 mm to 20.0 mm. Width: 14.0 mm to 16.0 mm. Shape: Egg shaped. Color: Mix of purple (RHS 187B and 77A) and green (RHS 146D).

*Petals.*—Arrangement: Open/free. Shape: Semi-circular. Apex: Rounded asymmetric. Margin: Entire. Length (from base to tip): 43.0 mm to 45.0 mm. Width: 53.0 mm to 55.0 mm. Color (when fully opened): Upper surface: Basic color: White (RHS 155C), dotted (dots are larger at the base and become smaller towards the edge) (RHS 187A and 59A) and edged (RHS 80B). Over color: Slightly light purple towards the apex (RHS 80B). Lower surface: Basic color: White (RHS 155C) with diluted purple dots (RHS 79B). Over color: Light purple (RHS 80B and 76C).

*Dorsal sepal.*—Shape: Elliptic. Apex: Emarginated symmetric. Margin: Entire. Length (from base to tip): 48.0 mm to 50.0 mm. Width: 31.0 mm to 33.0 mm. Color (when fully opened): Upper surface: Basic color: White (RHS 155C) dotted (dots are larger at the base and become smaller towards the edge) (RHS 187A and 59A) and edged (RHS 80B). Over color: Light purple towards the apex (RHS 80B). Lower surface: Basic color: Light purple (RHS 80B and 76C) with diluted purple edge and dots (RHS 77A and 79B). Over color: Purple at the base and apex (RHS 80B).

*Lateral sepals*.—Shape: Ovate. Apex: Obtuse asymmetric. Margin: Entire. Length (from base to tip): 46.0 mm to 48.0 mm. Width: 29.0 mm to 31.0 mm. Color (when fully opened): Upper surface: Basic color: White (RHS 155C) dotted (dots are larger at the base and become smaller towards the edge) (RHS 187A and 59A). Over color: Light green at the base (RHS 145D) and light purple towards the apex (RHS 80B). Lower surface: Basic color: Light purple (RHS 78B and 76C) with diluted purple dots (RHS 79A and 79B). Over color: Slightly green at the base (RHS 145C) and a purple apex (RHS 80B).

*Labellum* (*lip*).—Margin: Entire. Whiskers: Present. Length of whiskers: 7.0 mm to 9.0 mm. Color of whiskers: Purple (RHS 187A) with yellow tips (RHS 4C). Pubescence on the lip: Absent.

*Lateral lobe*.—Shape: Type IV (as described in the International Union for the Protection of New Varieties of Plants (UPOV) Test Guidelines for *Phalaenopsis*); spatulate. Length (from base to tip): 19.0 mm to 21.0 mm. Width: 12.0 mm to 14.0 mm. Color: White (RHS 155C) and yellow on one side (RHS 6A) dotted (RHS 80A) and at the base dark purple (RHS 187A).

*Apical lobe*.—Shape: Triangular. Length (from base to tip): 20.0 mm to 22.0 mm. Width: 23.0 mm to 25.0 mm. Color: White (RHS 155C) from whiskers purple (RHS 78A) with diluted dots (RHS 187B and 71A) and yellow at the base (RHS 5C and 5D).

*Callus*.—Average size: Medium. Height: 0.6 cm to 0.8 cm. Length: 0.5 cm to 0.7 cm. Width: 0.3 cm to 0.5 cm. Color: Dark greyed-purple (RHS 187A) and brown (RHS 200A) and white on the side (RHS 155C).

Reproductive organs:

*Arrangement*.—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column*.—Length: 8.0 mm to 10.0 mm. Diameter: 5.7 mm to 5.9 mm. Color: White (RHS 155C) and purple (RHS 80A).

*Pollinia*.—Quantity: 2. Size: 0.9 mm to 1.1 mm. Color: Yellow-orange (RHS 23A).

*Ovary*.—Part of the pedicel with small ribs towards the column. Length: 14.0 mm to 16.0 mm. Diameter: 3.0 mm to 3.2 mm.

*Pedicel*.—Length: 48.0 mm to 50.0 mm. Diameter: 3.5 mm to 3.8 mm. Color: From the inflorescence mix of greyed-purple (RHS 187B) and green (RHS 146C and 146D); light green (RHS 145C); light purple towards the flower (RHS 78D).

Disease, pest, and stress resistance: No specific resistance or susceptibility observed.

Temperature tolerance: Tolerant to a low temperature of 15° C. and a high temperature of about 30° C.

COMPARISON WITH PARENTAL AND COMMERCIAL VARIETIES

The female parent of 'PHALFOYX' is unknown, therefore a comparison cannot be made.

'PHALFOYX' differs from the male parent plant '00001-1920' (unpatented) in that 'PHALFOYX' has a flower that is dotted and edged, whereas '00001-1920' has a flower that is flecked. Additionally, 'PHALFOYX' has a triangular shaped apical lobe, whereas '00001-1920' has a trullate shaped apical lobe.

'PHALFOYX' differs from commercial variety 'PHALDISXO' (U.S. Plant Pat. No. 27,201) in that 'PHALFOYX' has a callus that is dark greyed-purple and brown and white on the side, whereas 'PHALDISXO' has a callus that is yellow-green with dark purple flecks. Additionally, 'PHALFOYX' has petals with a rounded apex and a dorsal sepal with an emarginated apex, whereas 'PHALDISXO' has petals with an emarginated apex and a dorsal sepal with an obtuse apex.

I claim:

1. A new and distinct variety of *Phalaenopsis* plant named 'PHALFOYX', substantially as described and illustrated herein.

* * * * *